US012383705B2

(12) United States Patent
Kokotoff et al.

(10) Patent No.: US 12,383,705 B2
(45) Date of Patent: Aug. 12, 2025

(54) BRIDLE DELIVERY SYSTEM HAVING REDUCED-CONTACT BRIDLE

(71) Applicant: Avent, Inc., Alpharetta, GA (US)

(72) Inventors: Sarah B. Kokotoff, Alpharetta, GA (US); Vernon Meadows, Lilburn, GA (US)

(73) Assignee: Avent, Inc., Alpharetta, GA (US)

( * ) Notice: Subject to any disclaimer, the term of this patent is extended or adjusted under 35 U.S.C. 154(b) by 85 days.

(21) Appl. No.: 17/386,748

(22) Filed: Jul. 28, 2021

(65) Prior Publication Data

US 2023/0031503 A1 Feb. 2, 2023

(51) Int. Cl.
*A61M 25/02* (2006.01)
*A61J 15/00* (2006.01)
*A61M 16/06* (2006.01)

(52) U.S. Cl.
CPC .......... *A61M 25/02* (2013.01); *A61J 15/0003* (2013.01); *A61M 16/0666* (2013.01);
(Continued)

(58) Field of Classification Search
CPC .......... A61M 25/02; A61M 2025/0226; A61M 2205/0272; A61M 16/0666; A61M 16/0461; A61M 16/0497; A61M 2210/0618; A61M 2210/1053; A61M 25/0127; A61M 2025/0213; A61M 16/0683; A61M 16/0488; A61M 25/00;
(Continued)

(56) References Cited

U.S. PATENT DOCUMENTS

| 4,480,639 A | 11/1984 | Peterson et al. |
| 4,634,425 A | 1/1987 | Meer |

(Continued)

FOREIGN PATENT DOCUMENTS

| DE | 102012203783 A1 | 3/2013 |
| EP | 0 609 020 A1 | 8/1994 |

(Continued)

OTHER PUBLICATIONS

Andrii Khomyshyn, Jewish Star of David icon. Vector six pointed stars symbol. May 23, 2019, Alamy.com, p. 1 (Year: 2019).*

(Continued)

*Primary Examiner* — Scott J Medway
*Assistant Examiner* — Anh Bui
(74) *Attorney, Agent, or Firm* — Meunier Carlin & Curfman LLC

(57) ABSTRACT

A securement device for a system for securing a nasal tube is provided. The securement device includes a bridle having a body extending between a first end and a second end. The body has a lobed or star shape. The securement device further includes a magnetic connection portion disposed at the first end of the bridle. A system for securing a nasal tube can include a securement device as described above, and a retrieval probe. The retrieval probe can include a catheter extending between a proximal end and a distal end; and a magnetic tip disposed at the proximal end. The magnetic connection portion of the bridle and the magnetic tip of the retrieval probe can be configured to magnetically couple during a procedure for inserting the bridle in a nasal passageway of a patient.

20 Claims, 3 Drawing Sheets

(52) U.S. Cl.
CPC .............. *A61M 2025/0226* (2013.01); *A61M 2205/0272* (2013.01)

(58) Field of Classification Search
CPC .............. A61M 25/01; A61M 16/0431; A61M 2039/0294; A61J 15/0003; A61J 15/0057
See application file for complete search history.

(56) References Cited

U.S. PATENT DOCUMENTS

| | | | |
|---|---|---|---|
| 4,671,287 A | 6/1987 | Fiddian-Green | |
| 4,778,448 A | 10/1988 | Meer | |
| 4,836,214 A | 6/1989 | Sramek | |
| 4,921,481 A | 5/1990 | Danis et al. | |
| 5,185,005 A * | 2/1993 | Ballantyne | A61M 25/02 604/179 |
| 5,399,165 A | 3/1995 | Paul, Jr. | |
| 5,660,168 A | 8/1997 | Ottosson et al. | |
| 5,897,521 A | 4/1999 | Lavigne | |
| 6,334,064 B1 | 12/2001 | Fiddian-Green | |
| 6,357,447 B1 | 3/2002 | Swanson et al. | |
| 6,464,668 B1 | 10/2002 | Pace | |
| 6,631,715 B2 | 10/2003 | Kirn | |
| 6,837,237 B2 | 1/2005 | Kirn | |
| 6,929,635 B2 | 8/2005 | Shelso | |
| 7,534,228 B2 | 5/2009 | Williams | |
| 7,695,459 B2 | 4/2010 | Gilbert et al. | |
| 7,803,137 B2 | 9/2010 | Stefanchik et al. | |
| 7,818,155 B2 | 10/2010 | Stuebe et al. | |
| 7,967,808 B2 | 6/2011 | Fitzgerald et al. | |
| 8,088,100 B2 | 1/2012 | Blix | |
| 8,147,486 B2 | 4/2012 | Honour et al. | |
| 8,177,773 B2 | 5/2012 | Ovcharchyn et al. | |
| 8,613,702 B2 | 12/2013 | Feer et al. | |
| 8,986,230 B2 | 3/2015 | Nishtala | |
| 9,114,066 B2 | 8/2015 | Kinpara | |
| 9,179,971 B2 | 11/2015 | Kirschenman | |
| 9,226,878 B2 | 1/2016 | Elia et al. | |
| 9,295,395 B2 | 3/2016 | Elia et al. | |
| 9,302,074 B2 | 4/2016 | Atkinson et al. | |
| 9,532,739 B2 | 1/2017 | Bennett-Guerrero | |
| 9,561,158 B2 | 2/2017 | Picha | |
| 9,610,227 B2 | 4/2017 | Elia | |
| 9,642,779 B2 | 5/2017 | Elia et al. | |
| 9,713,579 B2 | 7/2017 | Elia et al. | |
| 9,789,272 B2 | 10/2017 | Slaga et al. | |
| 9,943,335 B2 | 4/2018 | Gittard et al. | |
| 9,956,366 B2 | 5/2018 | Kirkpatrick et al. | |
| 10,004,875 B2 | 6/2018 | Bown et al. | |
| 10,314,994 B2 | 6/2019 | Phillips et al. | |
| 10,492,998 B2 | 12/2019 | Young | |
| 10,517,800 B2 | 12/2019 | Tatarek et al. | |
| 10,932,931 B2 | 3/2021 | Phillips | |
| 10,994,109 B2 | 5/2021 | Hakim et al. | |
| 11,045,617 B2 | 6/2021 | Bottom et al. | |
| 11,071,848 B2 | 7/2021 | Kirn et al. | |
| 2004/0069309 A1 | 4/2004 | Kirn | |
| 2005/0236001 A1 | 10/2005 | Williams | |
| 2006/0189947 A1 | 8/2006 | Gilbert et al. | |
| 2008/0097179 A1 | 4/2008 | Russo | |
| 2008/0167607 A1 | 7/2008 | Pfeiffer et al. | |
| 2008/0215002 A1 | 9/2008 | Rozenberg et al. | |
| 2008/0249467 A1 | 10/2008 | Burnett et al. | |
| 2010/0145147 A1 | 6/2010 | Pinsky et al. | |
| 2010/0294271 A1 | 11/2010 | Pttaway et al. | |
| 2012/0016256 A1 | 1/2012 | Mabary et al. | |
| 2012/0123328 A1 | 5/2012 | Williams | |
| 2012/0277619 A1 | 11/2012 | Starkebaum et al. | |
| 2013/0096482 A1 | 4/2013 | Bertrand et al. | |
| 2013/0225946 A1 | 8/2013 | Feer et al. | |
| 2013/0338521 A1 * | 12/2013 | Thompson | A61M 16/085 604/179 |
| 2014/0041666 A1 * | 2/2014 | Slaga | A61M 16/0683 128/207.18 |
| 2014/0196723 A1 * | 7/2014 | Kirkpatrick | A61M 25/01 128/207.18 |
| 2015/0157828 A1 * | 6/2015 | Phillips | A61M 16/0488 604/95.01 |
| 2016/0113843 A1 | 4/2016 | Elia et al. | |
| 2016/0129223 A1 | 5/2016 | Kirschenman | |
| 2016/0331298 A1 | 11/2016 | Burnett et al. | |
| 2017/0071502 A1 | 3/2017 | Bennett-Guerrero | |
| 2017/0202750 A1 | 7/2017 | Elia | |
| 2018/0078195 A1 | 3/2018 | Sutaria et al. | |
| 2018/0161249 A1 | 6/2018 | Elia et al. | |
| 2018/0289536 A1 | 10/2018 | Burnett | |
| 2019/0134349 A1 | 5/2019 | Cohn et al. | |
| 2019/0388068 A1 * | 12/2019 | Johnson | A61B 8/12 |
| 2020/0030558 A1 | 1/2020 | Avniel et al. | |
| 2020/0139064 A1 | 5/2020 | Hill | |
| 2020/0246588 A1 | 8/2020 | Akins et al. | |
| 2020/0282167 A1 | 9/2020 | Aardema et al. | |
| 2020/0405991 A1 | 12/2020 | Lenoard et al. | |
| 2021/0244482 A1 | 8/2021 | Tropello et al. | |

FOREIGN PATENT DOCUMENTS

| | | |
|---|---|---|
| GB | 2567870 B | 11/2019 |
| GB | 2532717 B | 7/2020 |
| JP | 2021053005 A | 4/2021 |
| WO | WO 92/17150 | 10/1992 |
| WO | WO 2008/010039 A2 | 1/2008 |
| WO | WO 2009/029869 A2 | 3/2009 |
| WO | WO 2015074602 A1 | 5/2015 |
| WO | WO 2020/256547 A1 | 12/2020 |

OTHER PUBLICATIONS

Lubo Ivanko, Rounded stars icon, version with four, five, six and seven points, Feb. 28, 2021, Alamy.com, p. 1 (Year: 2021).*

Definition of "Integrity" by Merrium-Webster; www.merrium-webster.com/dictionary/integrally; retrieved 2020. (Year: 2020).

International Search Report and Written Opinion for PCT/US2022/038480, dated Nov. 30, 2022, 15 pages.

* cited by examiner

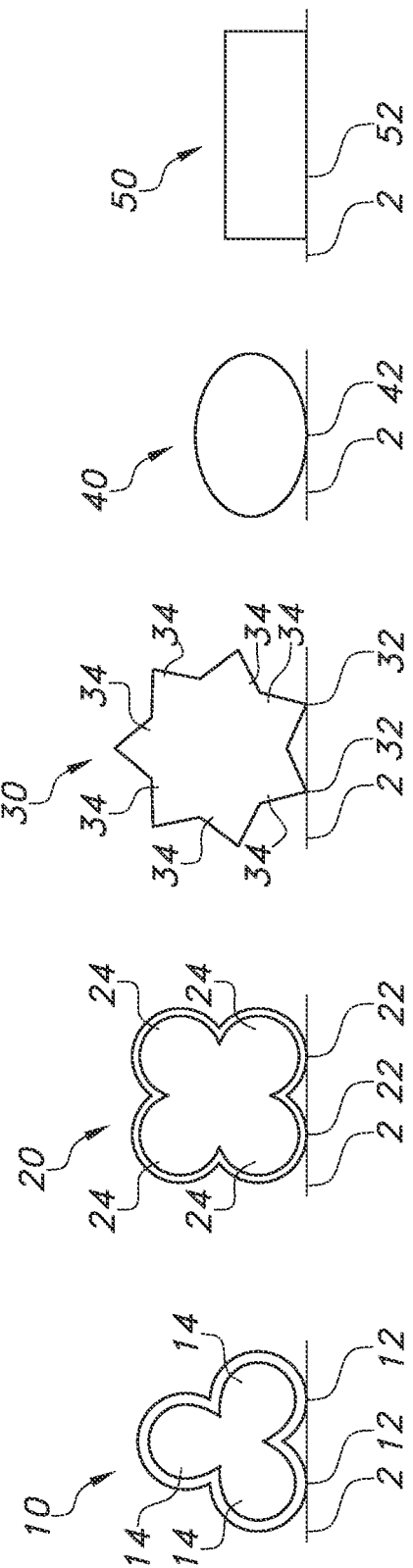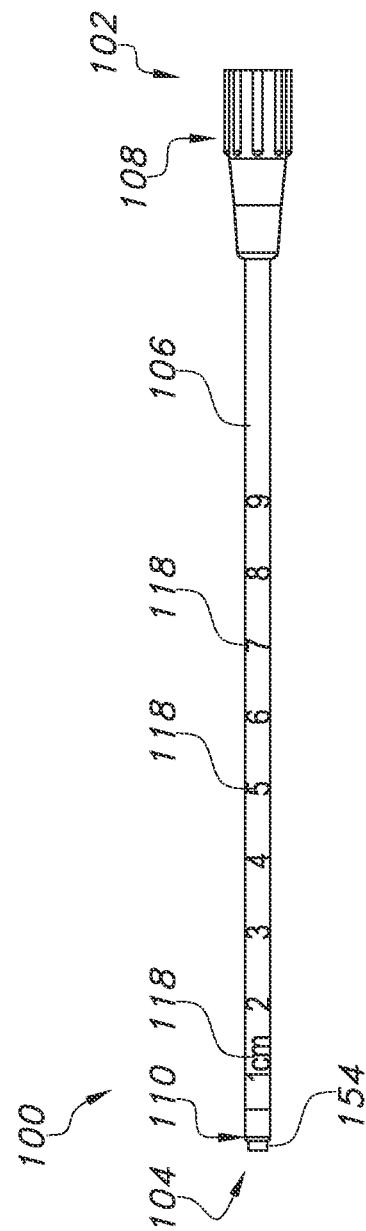

BRIDLE DELIVERY SYSTEM HAVING REDUCED-CONTACT BRIDLE

FIELD OF THE INVENTION

The subject matter of the present invention relates generally to a system for securing a nasal tube including a reduced-contact bridle.

BACKGROUND

The use of nasal tubes is commonly required in a medical setting, and many methods of securing nasal tubes that have been placed are known in the art. Generally, a nasal tube which has been inserted into a nostril may extend into a patient's stomach, intestinal tract, or lungs. Typically, once the nasal tube is in place, it is important to secure the tube. It should be appreciated that failing to properly secure a nasal tube can result in a dangerous situation for a patient, as well as increasing the cost of care, for example, by requiring repositioning of the nasal tube and re-securing the nasal tube.

There are various existing systems and methods for securing a nasal tube. For example, a nasal tube may be secured using a bridle being placed around the vomer bone. A clinician may place the bridle using a long flexible member, such as a tube, including the bridle and a magnet at the distal end, which is held together by the clinician's grasp. The long flexible member is inserted into one nostril, into the naval cavity towards the rear of the vomer bone. A retrieval probe with a magnet at the distal end is inserted into the other nostril to allow the magnets to contact each other around the vomer bone. Once the magnets have made contact, the clinician lets go of the bridle to allow the long flexible member to enter the nostril, and the probe is pulled outward, which pulls the long flexible member including the bridle around the vomer bone. With the bridle looped around the vomer bone and extending from both nostrils, the bridle may be secured with a clamp, which may have a channel to accept the nasal tube to secure the nasal tube. For example, the channel can have a smaller inside diameter than the outside diameter of the nasal tube, which provides for a tight fit of the nasal tube in the channel and allows the nasal tube to not fall out of the clamp prior to closing the clamp. The clinician may bring the clamp as close to the nostril as possible and press the tube into the tight channel in the clamp, place the bridle into the clamp, and close the clamp to secure the nasal tube to the bridle.

Existing nasal bridling devices for nasal tube securement typically rely on two catheters inserted into the nares past the vomer bone with magnets at the tip of each catheter to facilitate connection between the catheters behind the vomer bone and pass through of a tether through both nares. Typically, the first catheter may be the securement device or bridle, and the second catheter may be the retrieval probe. Existing bridle catheters typically rely on ribbon or tubular design profiles which reside in the nasal cavity when securing a nasal device. Such ribbon or tubular design profiles of the bridle catheter can allow for increased contact area with the surrounding delicate tissues of the nasal passageways. Additionally, the ribbon or tubular shaped bridle catheters can easily twist while in place within the nasal passageways. Some existing nasal bridle catheters can be formed from a polyester braid, which braided material can include openings therein in which bacteria may accumulate. Thus, such existing ribbon or tubular designs can increase the potential for tissue ulceration, infection, or necrosis, thereby potentially increasing medical costs, time of treatment, and pain for patients.

Consequently, there is a need for an improved bridle delivery system having a bridle with reduced contact area. In particular, an improved bridle delivery system that reduces the probability for twisting of the bridle would also be useful.

SUMMARY

Objects and advantages of the invention will be set forth in part in the following description, or may be obvious from the description, or may be learned through practice of the invention.

The present invention is directed to a securement device for a system for securing a nasal tube. The securement device includes a bridle having a body extending between a first end and a second end. The body comprises a lobed or star shape comprising a plurality of outer protrusions. The securement device further includes a magnetic connection portion disposed at the first end of the body of the bridle.

In one particular embodiment of the securement device, the body of the bridle can include a soft polymer.

In another embodiment, the body of the bridle can include a monofilament extending from the first end to the second end.

In an additional embodiment, the body of the bridle can include a solid core.

In a further embodiment, the plurality of outer protrusions comprises three outer protrusions.

In yet another embodiment, the outer protrusions can each have an approximately equal radius of curvature. Further, a ratio of a radius of the body of the bridle to the radius of curvature of the outer protrusions can be in a range from about 3:1 to about 5:1.

In still another embodiment, the body of the bridle can include at least one minor peak between each outer protrusion. Moreover, each minor peak can have a radius of curvature, further wherein a ratio of the radius of curvature of each minor peak to the radius of curvature of the outer protrusions can be in a range from 1.5:1 to about 3:1. Further, the bridle can include at least one valley disposed between each outer protrusion and the at least one minor peak.

In an additional embodiment, the magnetic connection portion can include a connecting member and magnetic connection member, wherein the magnetic connection member can include a permanent magnet or a material configured to magnetically couple to a permanent magnet that is not a permanent magnet. Moreover, the magnetic connection member can include an exposed end extending distally outward from a distal end of the connecting member. Further, the connecting member can be overmolded over the magnetic connection member. Moreover, the connecting member can be overmolded over a connection end of the body of the bridle.

The present invention is further directed to a system for securing a nasal tube. The system includes a bridle comprising a body extending between a first end and a second end, wherein the body comprises a lobed or star shape. The system further includes a magnetic connection portion attached to the bridle. The system further includes a retrieval probe. The retrieval probe includes a proximal end and a distal end; a catheter between the proximal end and the distal end; and a magnetic tip disposed at the proximal end. The magnetic connection portion of the bridle and the magnetic tip of the retrieval probe are configured to magnetically couple during a procedure for inserting the bridle in a nasal passageway of a patient.

In one particular embodiment of the system, either the magnetic connection portion of the bridle or the magnetic tip of the retrieval probe can include a permanent magnet. Moreover, the other of the magnetic connection portion of the bridle or the magnetic tip of the retrieval probe can include a magnetically connective material that is not a permanent magnet.

In another embodiment, the magnetic connection portion of the bridle and the magnetic tip of the retrieval probe each can include a permanent magnet.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 4A illustrates a cross-sectional view of a lobed-shape having three protrusions and two points of contact to a tangent line;

FIG. 4B illustrates a cross-sectional view of a lobed-shape having four protrusions and two points of contact to a tangent line;

FIG. 4C illustrates a cross-sectional view of a star-shape having seven protrusions and two points of contact to a tangent line;

FIG. 4D illustrates a cross-sectional view of an oval or tubular shape having a single elongated point of contact to a tangent line;

FIG. 4E illustrates a cross-sectional view of a ribbon-shape having a single elongated point of contact to a tangent line;

FIG. 5 illustrates a side view of an exemplary embodiment of a retrieval probe of the system for securing a nasal tube of the present invention.

DETAILED DESCRIPTION

Figure 1:
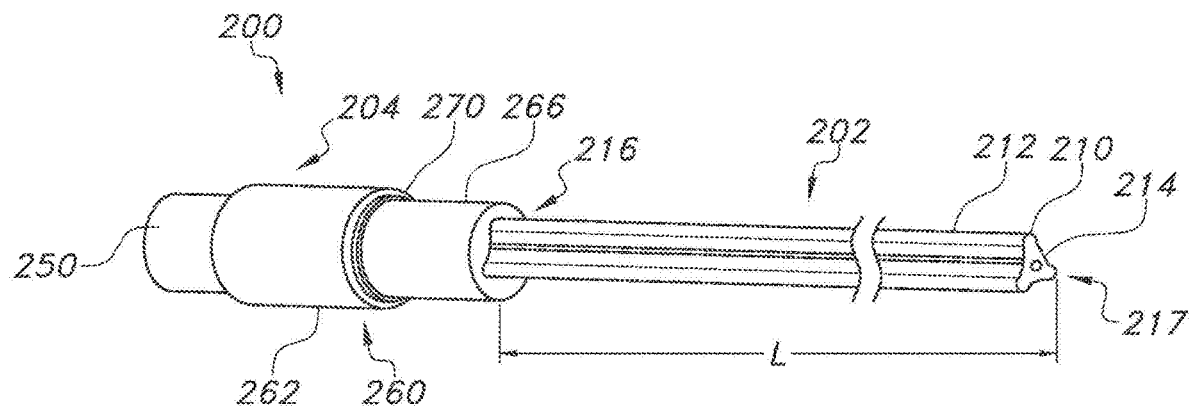
FIG. 1 illustrates a perspective view of a securement device including a bridle catheter according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to a securement device for a system for securing a nasal tube. The securement device includes a bridle having a body extending between a first end and a second end. The body has a lobed or star shape. The securement device further includes a magnetic connection portion disposed at the first end of the bridle. The present inventors have found that by providing a lobe or star shaped body of the bridle, both the size of contact area(s) between the body of the bridle and the patient's nasal tissues and the likelihood of twisting of the bridle can be reduced. In turn, the present inventors have found that the likelihood of abrasion, trauma, and necrosis of the patient's tissue resulting from contact between the bridle and the patient's tissue can be reduced. Additionally, the magnetic connection portion can have an exposed portion of magnetically connective material. The present inventors have found that the exposure of the magnetically connective connection member at the distal end of the retrieval probe increases the exposure of a magnetic surface to facilitate a stronger connection between the retrieval probe and a coupling member, such as a securement device, without sacrificing patient safety.

The specific features of the bridle securement device and the system for securing a nasal tube of the present invention may be better understood with reference to FIGS. 1-5.

Referring now to FIG. 1, one embodiment of a securement device 200 for a system for securing a nasal tube is shown. The securement device 200 includes a bridle (sometimes described as a "bridle catheter") 202 and a magnetic connection portion 204. The bridle 202 includes a body 210 having an outer surface 212. The body 210 can have a length L extending from a free end 217 to a connection end 216. The length L of the body 210 may be sufficiently long to extend through a first nare, around the vomer bone, through the second nare of a patient, and be secured, e.g., by tying, securement with a clip, or other means. For instance, the length L may be in a range from about 15 inches (38 cm) to about 30 inches (76 cm), such as from about 18 inches (46 cm) to about 28 inches (71 cm), for instance from about 20 inches (51 cm) to about 25 inches (64 cm). In a particular embodiment of the securement device 200, the body 210 can have a length L of about 22+/−0.25 inches (55.9+/−0.64 cm).

Figure 2:
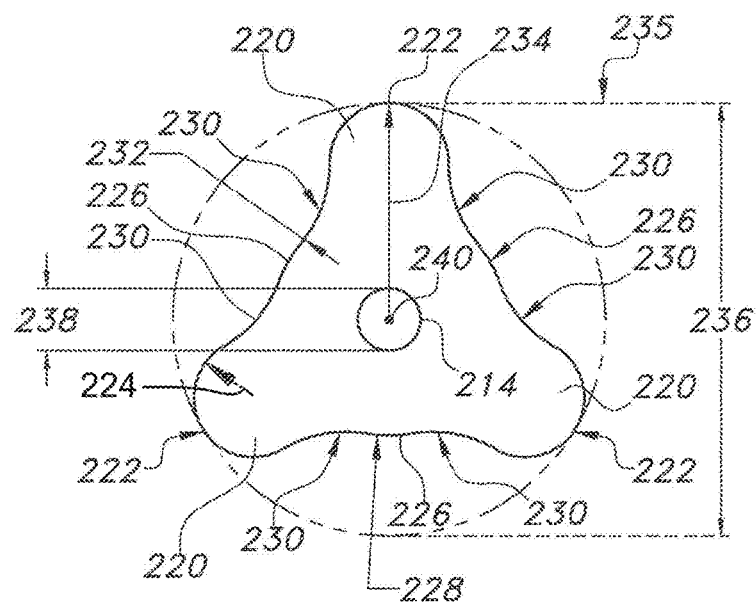
FIG. 2 illustrates a cross-sectional view of the bridle catheter of FIG. 1.

As shown in FIGS. 1 and 2, the body 210 of the bridle 202 may be formed with solid construction. In other words, the body 210 may not include any lumen(s) or open areas within the outer surface 212 of the body 210. For instance, the body 210 can be formed as a monofilament. Suitable materials for the body 210 of the bridle 202 include thermoplastic elastomers such as polyolefins, including polyethylene and polypropylene, polyamides, polyimides, teflon (polytetrafluoroethylene), polyesters, polyurethanes, any copolymers thereof, and other materials known in the art. In some particular embodiments, the body 210 can be formed from a soft (i.e., non-rigid) polymer, for example polyurethane and/or a polyurethane blend. The solid construction of the body 210 of the bridle 202 can be formed, e.g., by extrusion. For instance, in some aspects of the invention, a solid inner core 214 having, e.g., a cylindrical shape, can be extruded and the body 210 of the bridle 202 can be extruded over the inner core 214.

The present inventors have found that forming the bridle 202 as a monofilament of solid construction may reduce the risk of bacterial accumulation along the bridle 202 as compared to existing nasal bridles formed of a tubular or braided construction. In particular, because the solid monofilament construction does not include any openings, apertures or other unexposed surfaces, the likelihood of bacteria growing alongside the bridle 202 may be reduced. In contrast, existing nasal bridles of tubular construction can potentially allow bacteria to enter or grow within an inner lumen of the tubular construction. Similarly, existing nasal bridles formed from a braided construction are formed with many crevices between pieces of braided material along outer and inner surfaces of the bridle, forming many surfaces and crevices in which bacteria may colonize.

The outer surface 212 of the body 210 of the bridle 202 can have a shape defining at least three protrusions 220. For instance, the outer surface 212 of the body 210 can have a lobed shape or a star shape. In a particular embodiment of the present invention illustrated in FIGS. 1-2, the outer surface 212 of the body 210 can have a tri-lobed shape having three outer protrusions 220. The outer protrusions 220 can be substantially equally spaced around a center point 240 of the body 210. Each outer protrusion 220 can include an outermost contact point 222 at a point of the outer protrusion 220 on the outer surface 212 furthest from the center point 240. The body 210 of the bridle 202 can have a radius 234 extending from the center point 240 to a contact point 222 of each outer protrusion 220. The radius 24 can be approximately equal within each respective outer protrusion 220. The radius 234 can be in a range from about 0.015 inches (0.38 mm) to about 0.055 inches (1.40 mm), such as from about 0.02 inches (0.51 mm) to about 0.05 inches (1.27 mm), for instance from about 0.03 inches (0.76 mm) to about 0.04 inches (1.02 mm). Each of the contact points 222 can be connected by an imaginary circle 235 extending around the body 210. The imaginary circle 235 can have a diameter 236 in a range from about 0.04 inches (1.02 mm) to about 0.1 inches (1.54 mm), such as from about 0.05 inches (1.27 mm) to about 0.09 inches (2.29 mm), such as from about 0.06 inches (1.52 mm) to about 0.08 inches (2.03 mm). Importantly, the radius 234 extending from the center point 240 to a contact point 222 can be equal to the radius (i.e., one half of the diameter 236) of the imaginary circle 235.

At the contact point 222 of each outer protrusion 220, the outer protrusion 220 can have a radius of curvature 224. The radius of curvature 224 of the outer protrusion 220 can be in a range from about 0.005 inches (0.13 mm) to about 0.015 inches (0.38 mm), such as from about 0.007 inches (0.18 mm) to about 0.012 inches (0.30 mm), for instance from about 0.008 inches (0.20 mm) to about 0.01 inches (0.25 mm).

A ratio of the radius 234 of the body 210 to the radius of curvature of the 224 of the outer protrusions 220 can be in a range from about 3:1 to about 5:1, such as from about 3.25:1 to about 4.5:1, for instance from about 3.5:1 to about 4.25:1. By providing outer protrusions 220 that have a significantly smaller radius of curvature 224 than the body 210, e.g., about three to five times smaller, the area of the contact points 222 which may contact the patient's tissues can be substantially reduced, as compared to a tubular (e.g., circular) or ribbon-shaped (e.g., rectangular) bridle. As a result, the possibility of tissue damage due to abrasion between the bridle 202 and the patient's tissue can be minimized.

Additionally, as best illustrated in FIG. 2, between outer protrusions 220, the outer surface 212 of the body 210 of the bridle 202 may include a minor peak 226. Further, a valley 230 may be formed between each minor peak 226 and protrusion 220. In some aspects of the invention, there can be a minor peak 226 in between each outer protrusion 220. By providing a minor peak 226 between each outer protrusion 220, the depth of the valleys 230 can be minimized such that there is less space for debris or buildup, e.g., bacteria, to accumulate between the outer protrusions 220. The minor peaks 226 can each have a radius of curvature 228 in a range from about 0.015 inches (0.38 mm) to about 0.022 inches (0.56 mm), such as from about 0.016 inches (0.41 mm) to about 0.021 inches (0.53 mm), for instance from about 0.017 inches (0.43 mm) to about 0.019 inches (0.48 mm). The valleys 230 can each have a radius of curvature 232 in a range from about 0.016 inches (0.41 mm) to about 0.025 inches (0.64 mm), such as from about 0.018 inches (0.46 mm) to about 0.022 inches (0.56 mm), for instance from about 0.019 inches (0.48 mm) to about 0.021 inches (0.53 mm).

A ratio of the radius of curvature 228 of the minor peaks 226 to the radius of curvature 232 of the valleys 230 can be in a range from about 0.75:1 to about 1:1, for instance about 0.9:1. Additionally, a ratio of the radius of curvature 228 of the minor peaks 226 to the radius of curvature 224 of the outer protrusions 220 can be in a range from about 1.5:1 to about 3:1, for instance about 2:1.

Figure 3:
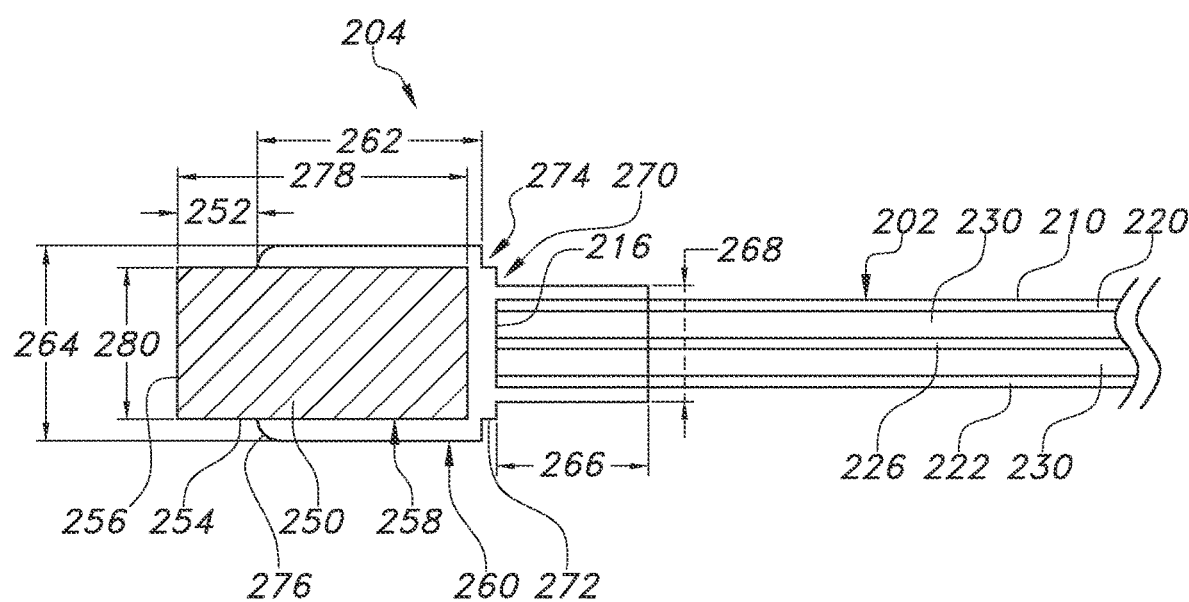
FIG. 3 illustrates a side cut-away view of the securement device of FIG. 1.

As illustrated in FIGS. 4A-E, a lobed or star-shaped design can result in providing at least two contact points along a surface. For instance, a tri-lobed shape 10 similar to that of the body 210 of the bridle 202 shown in FIGS. 1-3 is illustrated in FIG. 4A. The tri-lobed shape 10 includes three protrusions 14. On a contact surface 2, e.g., analogous to a patient's tissue, the tri-lobed shape 10 can have two contact points 12 with the contact surface 2. Similarly, FIG. 4B illustrates a lobed shape 20 having four protrusions 24 which forms two contact points 22 on a surface 2. In a similar manner, FIG. 4C illustrates a star shape 30 having seven protrusions (points) 34 and two contact points 32 on the surface 2. In contrast, the tubular shape 40 shown in FIG. 4D includes a single contact point 42 on the surface 2 at a point along a surface of the tubular shape. FIG. 4E further illustrates a ribbon-shape, e.g., a rectangle, 50 which has a single contact plane 52 along the surface 2 that extends an entire length of a side of the rectangle. In comparison to the shapes illustrated in FIGS. 4A-D, the ribbon or rectangular shape 50 shown in FIG. 4E has the largest contact surface. In a bridle formed with the shape 50, the bridle would have an expansive contact area with a patient's tissue, which may cause more abrasion with the patient's tissue in an undesirable manner.

Moreover, the present inventors have found that providing a lobed or star shaped construction for the body 210 of the bridle 202 can reduce twisting of the body 210 of the bridle 202. In particular, the solid construction of the lobed or star shape can resist twisting around a longitudinal axis (e.g., an axis formed through the center point 240). Thus, in a circumstance in which the body 210 of the bridle 202 becomes twists, the body 210 is likely to inherently right itself due to the shape of the body 210 resisting the twisting forces.

Turning now to FIG. 3, the magnetic connection portion 204 of the securement device 200 is illustrated in further detail. A connecting member 260 is provided which connects the connection end 216 of the bridle 202 to a magnetic connection member 250 such as a permanent magnet. The connecting member 260 can include a bridle portion 266 in which the connection end 216 of the bridle 202 can be disposed. The bridle portion 266 may have a diameter 268. The diameter 268 of the bridle portion 266 may be greater than the diameter 236 of the imaginary circle 235 that circumscribes the contact points 222 of the bridle 202. In some aspects of the present invention, the bridle portion 266 can be overmolded over the connection end 216 of the bridle 202 to permanently couple the connecting member 260 and the bridle 202; however, any suitable method of attaching the connecting member 260 to the bridle 202 can be used.

At an opposite end of the magnetic connection portion 204 from the bridle portion 266, the magnetic connection portion 204 includes a magnet portion 262. The magnetic connection member 250 can be disposed within the magnet portion 262. For instance, the magnetic connection member 250 can be formed from a permanent magnet, a rare earth magnet, or any suitable material to provide for magnetic coupling with a cooperating magnetic coupling. The magnetic connection member 250 can have a generally cylindrical shape having a diameter 280. The diameter 280 can be in a range from about 0.09 inches (about 2.3 mm) to about 0.11 inches (about 2.8 mm), such as about 0.1 inches (about 2.5 mm).

The magnetic connection member 250 includes an enclosed portion 258 disposed within the connecting member 260 and an exposed section 252 which extends beyond a distal end 276 of the connecting member 260. The exposed section 252 of the magnetic connection member 250 can include a lateral surface 254 and an end surface 156 disposed generally perpendicular to the lateral surface 254. The exposed section 252 can have an axial length along the lateral surface 254 in a range from about 0.03 inches (about 0.6 mm) to about 0.1 inches (about 2.5 mm), such as from about 0.04 inches (about 1 mm) to about 0.07 inches (about 1.8 mm), such as from about 0.045 inches (about 1.1 mm) to about 0.055 inches (about 1.4 mm). The magnetic connection member 250 can have an overall length 278 in a range from about 0.12 inches (about 3.05 mm) to about 0.25 inches (about 6.35 mm), such as from about 0.15 inches (about 3.81 mm) to about 0.2 inches (about 5.08 mm), for instance, from about 0.18 inches (about 4.57 mm) to about 0.192 inches (about 4.88 mm).

A ratio of the length of the exposed section 252 to an overall length 278 of the magnetic connection member 250 can be in a range from about 1:5 to about 1:2, such as from about 1:4 to about 1:3. Notably, the length of the exposed section 252 may be generally about two to three times larger than a length of an exposed section of magnet of prior art bridle connection devices. The present inventors have found that the increased length of the exposed section 252 of the magnetic connection portion 204 of the securement device 200 of the present invention can allow for overall increased exposure of the magnetically connective surface of the magnetic connection portion 204 along the lateral surface 254, thereby facilitating a stronger magnetic connection between the magnetic connection portion 204 of the securement device 200 and a cooperating device, such as a retrieval probe, without compromising patient safety.

The magnet portion 262 of the connecting member 260 can have a diameter 264 that is greater than the diameter 280 of the magnetic connection member 250 such that the magnet portion 262 surrounds the magnetic connection member 250 along the length of the magnet portion 262. In some aspects of the present invention, the magnet portion 262 can be overmolded over the magnetic connection member 250 to permanently couple the magnet portion 262 and the magnetic connection member 250; however, any suitable method of attaching the magnetic connection member 250 can be used.

Moreover, as shown in FIG. 3, the diameter 264 of the magnet portion 262 can be greater than the diameter 268 of the bridle portion 266. Further, the connecting member 260 can have an intermediate portion 272 disposed between the magnet portion 262 and the bridle portion 266. A diameter of the intermediate portion 272 of the connecting member 260 can be different from the diameter 264 of the magnet portion 262 and the diameter 268 of the bridle portion 266. Moreover, as shown in FIG. 3, the connecting member 260 may include a first shoulder 270 disposed between the bridle portion 266 and the intermediate portion 272, and a second shoulder 274 disposed between the intermediate portion 272 and the magnet portion 266. The first shoulder 270 and second shoulder 274 can form a stepped, e.g., step-up or step-down, configuration along the connecting member 260. However, in other aspects of the invention, the connecting member 260 may have a tapered diameter along all or a portion of its length. A tapered configuration may be combined with the stepped arrangement described above. Moreover, in further aspects of the present invention, the connecting member 260 may have a constant diameter along its length such that the diameter 264 of the magnet portion 262 and the diameter 268 of the bridle portion 266 are the same.

As shown in FIG. 3, the connecting member 260 can be formed of unitary, i.e., one-piece, construction to attach the magnetic connection member 250 to the connection end 216 of the bridle 202. For instance, the connecting member 260 can be an overmolded structure that is overmolded over both the connection end 216 of the bridle 202 and the magnetic connection member 250. In some aspects, the connecting member 260 can be simultaneously overmolded over both the connection end 216 of the bridle 202 and the magnetic connection member 250. The connecting member 260 can be formed of any suitable material. For instance, in some aspects of the present invention the connecting member 260 may be formed from polyvinyl acetate (PVA).

Turning now to FIG. 5, an exemplary retrieval probe 100 is illustrated. The retrieval probe 100 may be a part of the system for securing a nasal tube of the present invention. The retrieval probe 100 can include an elongated member 106 that extends between a proximal end 102 and a distal end 104. The retrieval probe 100 includes a handle 108 at the proximal end 102, and a magnetic tip 110 at the distal end 104. The elongated member 106 of the retrieval probe 100 may be approximately 5 inches (about 12.7 cm) long, with the handle 108 being approximately 1 inch (about 2.54 cm) long. A magnetic tip 110 can be disposed at the distal end 104 of the retrieval probe 100. The magnetic tip 110 can include a connection member 154, e.g., a magnet or a magnetically connective material. The connection member 154 can be formed from a permanent magnet, a rare earth magnet, or any suitable material to provide for magnetic coupling with a cooperating magnetic coupling. For instance, when the securement device 200 includes a magnetic connection member 250 formed from a permanent magnet, the connection member 154 can be formed from a permanent magnet having opposite polarity, or a material configured to magnetically couple to a permanent magnet that is not a permanent magnet. An example of such material can be stainless steel or any other suitable material having low magnetic reluctance. Alternatively, when the connection member 154 includes a permanent magnet, the magnetic connection member 250 of the retrieval probe of the present invention can be formed from a material configured to magnetically couple to a permanent magnet that is not a permanent magnet, such as stainless steel.

In use, the securement device 200 can be inserted into a first nostril, e.g., by inserting the securement device 200 within a delivery probe (not shown) and inserting the delivery probe into the first nostril. The magnetic connection portion 204 of the securement device 200 can be inserted towards the rear of the vomer bone of a patient through the first nostril. Then, the retrieval probe 100 can be inserted into a second nostril, with the connection member 154 exposed at the distal end 102 of the retrieval probe 100 and inserted towards the rear of the vomer bone of the patient within the second nostril. The magnetic connection portion 204 of the securement device 200 and the connection member 154 of the retrieval probe 100 can be magnetically coupled behind the patient's vomer bone. For instance, the body 210 of the bridle 202 and/or the elongated member 106 of the retrieval probe 100 can bend or flex behind the vomer bone as the magnetic attraction between the connection member 154 and the magnetic connection portion 204 increases to bring the connection member 154 and the magnetic connection portion 204 together. After the magnetic connection portion 204 and the connection member 154 are coupled, the retrieval probe 100 is removed from the second nostril, such that the body 210 of the bridle 202 extends into the first nostril and out from the second nostril. If applicable, the delivery probe is then removed from the first nostril. For example, when the retrieval probe 100 is removed from the second nostril, the body 210 of the bridle 202 is left hanging out of both nostrils. Then, the bridle 202 can be secured using any suitable means. Moreover, a nasal tube can be inserted and/or secured to the bridle using any suitable means to secure the nasal tube within the patient's nose and deter or discourage the patient from pulling on the nasal tube.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A securement device for a system for securing a nasal tube comprising:
   a bridle having a body extending between a first end and a second end, wherein the body comprises a lobed shape comprising at least three outer protrusions about a circumference of the body; and
   a magnetic connection portion disposed at the first end of the body of the bridle;
   wherein the body of the bridle comprises at least one minor peak between each outer protrusion; and
   wherein an outer diameter of the body defined at the minor peak is less than an outer diameter of the body defined at the outer protrusions.

2. The securement device of claim 1, wherein the body of the bridle comprises a soft polymer.

3. The securement device of claim 1, wherein the body of the bridle comprises a monofilament extending from the first end to the second end.

4. The securement device of claim 1, wherein a cylindrical inner core is composed of a solid material and integrally coupled to the body of the bridle.

5. The securement device of claim 1, wherein the at least three outer protrusions comprises exactly three outer protrusions.

6. The securement device of claim 1, wherein the at least three outer protrusions each have an approximately equal radius of curvature.

7. The securement device of claim 6, wherein of a radius of the body of the bridle is greater than to the radius of curvature of the at least three outer protrusions such that a contact area defined by the radius of curvature of the body is reduced.

8. The securement device of claim 1, wherein each minor peak has a radius of curvature greater than a radius of curvature of the at least three outer protrusions.

9. The securement device of claim 1, further comprising at least one valley disposed between each outer protrusion and the at least one minor peak.

10. The securement device of claim 1, wherein the magnetic connection portion comprises a connecting member and a magnetic connection member, wherein the magnetic connection member comprises a permanent magnet or a material configured to magnetically couple to a permanent magnet that is not a permanent magnet.

11. The securement device of claim 10, wherein the magnetic connection member comprises an exposed end extending distally outward from a distal end of the connecting member,
   wherein an outer surface of the connecting member includes a first shoulder and a second shoulder forming a decreasing stepped surface extending longitudinally between the magnetic connection member and the body of the bridle.

12. The securement device of claim 10, wherein the connecting member is overmolded over the magnetic connection member,
   wherein the connecting member is overmolded over the magnetic connection member.

13. The securement device of claim 10, wherein the connecting member is overmolded over a connection end of the body of the bridle.

14. A system for securing a nasal tube comprising:
   a bridle comprising a body extending between a first end and a second end, wherein the body comprises a lobed shape having at least three outer protrusions about a circumference of the body, wherein the body of the bridle comprises at least one minor peak between each outer protrusion; and wherein an outer diameter of the body defined at the minor peak is less than an outer diameter of the body defined at the outer protrusions;
   a magnetic connection portion attached to the bridle; and
   a retrieval probe, the retrieval probe comprising:
      a proximal end and a distal end;
      a catheter between the proximal end and the distal end; and
      a magnetic tip disposed at the proximal end,
   wherein the magnetic connection portion of the bridle and the magnetic tip of the retrieval probe are configured to magnetically couple during a procedure for inserting the bridle in a nasal passageway of a patient.

15. The system of claim 14, wherein either the magnetic connection portion of the bridle or the magnetic tip of the retrieval probe comprises a permanent magnet.

16. The system of claim 15, wherein the other of the magnetic connection portion of the bridle or the magnetic tip of the retrieval probe comprises a magnetically connective material that is not a permanent magnet.

17. The system of claim 14, wherein the magnetic connection portion of the bridle and the magnetic tip of the retrieval probe each comprises a permanent magnet.

18. The system of claim 14, the magnetic connection portion comprising a magnetic connection member partially extending beyond a connecting member, wherein a ratio of a length of an exposed section of the magnetic connection member to an overall length of the magnetic connection member is a range from about 1:5 to about 1:2.

19. The securement device of claim 1, wherein the three outer protrusions are configured to resist twisting of the body around a longitudinal axis of the body.

20. The securement device of claim 1, wherein the body is of solid construction and does not define any openings or apertures;
- wherein the at least three outer protrusions have a semi-circular cross-sectional shape and extend parallel to a longitudinal axis of the body, the outer protrusions extending between the first end and the second end of the body;
- wherein the body comprises a cylindrical inner core extending between the first end and the second end along the longitudinal axis; and
- wherein the body defines a smooth outer surface and resists bacterial accumulation.

\* \* \* \* \*

UNITED STATES PATENT AND TRADEMARK OFFICE
CERTIFICATE OF CORRECTION

Page 1 of 1

| | |
|---|---|
| PATENT NO. | : 12,383,705 B2 |
| APPLICATION NO. | : 17/386748 |
| DATED | : August 12, 2025 |
| INVENTOR(S) | : Sarah B. Kokotoff and Vernon Meadows |

It is certified that error appears in the above-identified patent and that said Letters Patent is hereby corrected as shown below:

In the Claims

Column 10, Line 16:
Please delete:
"than to"
Please insert:
-- than --

Signed and Sealed this
Twenty-first Day of October, 2025

John A. Squires
*Director of the United States Patent and Trademark Office*